(12) United States Patent
Pease et al.

(10) Patent No.: US 7,758,495 B2
(45) Date of Patent: *Jul. 20, 2010

(54) REMOTE INSPECTION DEVICE (75) Inventors: Alfred A. Pease, Ann Arbor, MI (US); Al Boehnlein, Ypsilanti, MI (US); Tye Newman, Howell, MI (US); Paul J. Eckhoff, Fenton, MO (US)

(73) Assignee: Perceptron, Inc., Plymouth, MI (US)

( * ) Notice: Subject to any disclaimer, the term of this patent is extended or adjusted under 35 U.S.C. 154(b) by 1150 days.

This patent is subject to a terminal disclaimer.

(21) Appl. No.: 11/328,603

(22) Filed: Jan. 10, 2006

(65) Prior Publication Data
US 2006/0167340 A1 Jul. 27, 2006

Related U.S. Application Data (63) Continuation-in-part of application No. 11/032,275, filed on Jan. 10, 2005, now abandoned.

(51) Int. Cl.
*A61B 1/00* (2006.01)
*A61B 1/04* (2006.01)

(52) U.S. Cl. .................................... 600/104; 600/129
(58) Field of Classification Search ................. 600/101, 600/104, 127, 129, 137
See application file for complete search history.

(56) References Cited

U.S. PATENT DOCUMENTS

| | | | |
|---|---|---|---|
| 3,066,969 A | 12/1962 | Camac | |
| 4,467,802 A | 8/1984 | Maslanka | |
| 4,471,766 A | 9/1984 | Terayama | |
| 4,779,130 A | 10/1988 | Yabe | |
| 5,053,043 A * | 10/1991 | Gottesman et al. | 606/148 |
| 5,433,725 A | 7/1995 | Christian et al. | |
| 5,464,008 A * | 11/1995 | Kim | 600/157 |
| 5,667,473 A | 9/1997 | Finn et al. | |
| 5,681,262 A * | 10/1997 | Isse | 600/127 |
| 5,752,973 A | 5/1998 | Kieturakis | |
| 5,910,105 A * | 6/1999 | Swain et al. | 600/131 |
| 5,928,137 A * | 7/1999 | Green | 600/160 |
| 5,986,752 A | 11/1999 | Morito et al. | |
| 6,059,719 A * | 5/2000 | Yamamoto et al. | 600/127 |
| 6,071,233 A * | 6/2000 | Ishikawa et al. | 600/104 |
| 6,086,528 A | 7/2000 | Adair | |
| 6,091,453 A | 7/2000 | Coan et al. | |
| 6,118,476 A | 9/2000 | Morito et al. | |
| 6,221,007 B1 | 4/2001 | Green | |
| 6,369,849 B1 | 4/2002 | Rzynski | |
| 6,419,626 B1 * | 7/2002 | Yoon | 600/109 |

(Continued)

*Primary Examiner*—John P Leubecker
*Assistant Examiner*—Philip R Smith
(74) *Attorney, Agent, or Firm*—Harness, Dickey & Pierce, P.L.C.

(57) ABSTRACT

An integrated solid state device for viewing and manipulating objects located in remote sites and locations which includes a flexible cable having a camera on one end and a viewer on an opposite end. The camera captures images near the end of the flexible cable and converts the images into a video signal that is transferred through wires that extend through the length of the flexible cable. The video signals are received by the viewer and converted into a displayed image. A variety of removable article manipulators can be attached to the distal end of the flexible cable and used to manipulate, capture and retrieve articles and objects near the distal end of the flexible cable.

21 Claims, 8 Drawing Sheets

U.S. PATENT DOCUMENTS

| | | | |
|---|---|---|---|
| 6,419,627 B1 * | 7/2002 | Ben Nun | 600/125 |
| 6,577,339 B1 | 6/2003 | Thompson et al. | |
| 6,692,432 B1 | 2/2004 | Yarush et al. | |
| 7,009,698 B2 | 3/2006 | Drost et al. | |
| 7,179,223 B2 * | 2/2007 | Motoki et al. | 600/131 |
| 7,384,308 B2 * | 6/2008 | Boehnlein et al. | 439/585 |
| 7,485,092 B1 * | 2/2009 | Stewart et al. | 600/127 |
| 2001/0026315 A1 | 10/2001 | Ooshima et al. | |
| 2003/0035048 A1 | 2/2003 | Shipp | |
| 2003/0050534 A1 * | 3/2003 | Kazakevich | 600/178 |
| 2003/0114839 A1 * | 6/2003 | Looper et al. | 606/1 |
| 2004/0054254 A1 * | 3/2004 | Miyake | 600/104 |
| 2004/0193007 A1 | 9/2004 | Martone et al. | |
| 2004/0242958 A1 * | 12/2004 | Fujikawa et al. | 600/102 |
| 2005/0070764 A1 * | 3/2005 | Nobis et al. | 600/131 |
| 2005/0143626 A1 * | 6/2005 | Prescott | 600/162 |
| 2006/0004258 A1 * | 1/2006 | Sun et al. | 600/160 |

* cited by examiner

REMOTE INSPECTION DEVICE

RELATED APPLICATIONS

The present invention is a Continuation-In-Part of U.S. patent application Ser. No. 11/032,275, filed Jan. 10, 2005 now abandoned of which the entire specification is expressly incorporated herein by reference and to which priority is claimed under 35 U.S.C. §120.

TECHNICAL FIELD

The present invention relates to an optical device for observing remote sites and locations that have limited access. More specifically, the present invention is directed to an optical device that can be used for observing, manipulating and retrieving objects in remote sites and locations which optical device can include different attachments and configurations.

BACKGROUND ART

When inspecting the interior of engine cylinders at automotive equipping plants, repair shops, etc., a borescope is commonly inserted through a spark plug hole and used to inspect the interior of a cylinder without going through all the trouble of removing the engine's cylinder head(s). Borescopes are also used in the aviation industry, in marinas and shipyards, and in many other facilities in which various mechanical machines and devices are fabricated, assembled and/or repaired. Similar optical scopes are used to inspect the interior of scuba and gas storage tanks. Other fields in which borescopes or similar optical scopes are used include plumbing, mining, rescue, monitoring, and police investigations, to name only a few.

Borescopes and similar optical scopes commonly use cables that are formed from coherent bundles of optical fibers. Coherent bundles mean that the spatial relationship of individual each fiber to all the other fibers has to be maintained at each end of the cable. Since each fiber is essentially a "pixel," it is necessary to maintain the spatial relationship of the fibers. This requirement contributes to the high cost of borescopes and similar optical scopes that use optical fiber cables.

In borescopes and similar optical scopes a lens is provided at the front end of the fiber bundles which focuses an image of what is being observed onto the polished ends of the fibers in the fiber bundle. A view lens is provided at the opposite end of the fiber bundle which transfers the relatively course image produced at the front end of the device to an observer using the device.

When using borescopes and similar optical scopes objects in dark areas illumination is commonly provided by means of a strong and relatively expensive halogen light source projected down the cable from the observation end. The light source used for illumination has to be strong due to the fact the light has to be transmitted from one end of the cable to the other and onto an objected to be imaged and then the image has to be transmitted back through the cable to be observed.

The present invention provides optical devices for observing, manipulating and retrieving objects in remote sites and locations, which optical devices include a variety of attachments and configurations.

DISCLOSURE OF THE INVENTION

According to various features, characteristics and embodiments of the present invention which will become apparent as the description thereof proceeds, the present invention provides an optical device for observing a remote situs which includes:

a length of flexible cable having a distal end and a proximal end;

an imager coupled to the distal end of the flexible cable for obtaining an image beyond the distal end of the flexible cable and converting the image into an electrical video signal;

a handheld image viewer coupled to the proximal end of the flexible cable for receiving the electrical video signal and converting the electrical video signal into a viewable image;

electrical leads that extend between the distal and proximal ends of the flexible cable to transfer the electrical video signal from the imager to the image viewer; and at least one article manipulation attachment that is removably coupled to the distal end of the flexible cable for manipulating an object located near the distal end of the flexible cable.

The present invention further provides a kit for locating and manipulating various objects located in remote situs which includes:

a length of flexible cable having a distal end and a proximal end;

an imager coupled to the distal end of the flexible cable for obtaining an image beyond the distal end of the flexible cable and converting the image into an electrical video signal;

a handheld image viewer coupled to the proximal end of the flexible cable for receiving the electrical video signal and converting the electrical video signal into a viewable image;

electrical leads that extend between the distal and proximal ends of the flexible cable to transfer the electrical video signal from the imager to the image viewer; and a set of article manipulation attachments that can be removably and interchangeably coupled to the distal end of the flexible cable for manipulating an object located near the distal end of the flexible cable.

BRIEF DESCRIPTION OF DRAWINGS

The present invention will be described with reference to the attached drawings which are given as non-limiting examples only, in which.

BEST MODE FOR CARRYING OUT THE INVENTION

The present invention is directed to solid state optical snake devices for observing and/or manipulating and/or retrieving objects in remote sites or locations which can be used with a number of attachments that are designed and configured to manipulate and/or retrieve various objects that, due to their presence in remote situs, are otherwise inaccessible.

The reference to "solid state" as used herein is intended to distinguish the present optical devices from known optical devices that include optical fiber bundles as discussed above. Rather than use an optical fiber bundle, the optical devices of the present invention use a flexible cable through which signal transmitting wires extend and which flexible cable provides support for a number of different attachments that can be removably coupled and interchanged on the distal end of the optical devices.

In addition to being configured to support a number of different attachments, the distal end of the flexible cable is coupled to a housing which contains an electronic imager, such as a CMOS or CCD imager or some other type of camera, including digital cameras, that can be monochrome, color or infrared imagers.

According to various embodiments, the removable attachments can include various configured hooks, baskets, nets, magnets, spears, lances, grapple or snagging devices, observational mirrors, etc. which can be manipulated to capture and retrieve various articles and/or manipulate various articles within remote situs.

The attachments are configured to be coupled to the distal end of the cable in any convenient manner which will allow the attachments to be removed, replaced and/or interchanged. According to one embodiment the attachments are provided with engaging structures such as clips that are configured to be attached to the distal end of the cable such as on a portion of the housing which can be configured to engagingly receive such clips. In alternative embodiments, any type of connecting structure can be incorporated and used to attach the attachments to the distal end of the flexible cable including for example, bayonet mounting structures, lour-locking structures, threaded connections, locking rings, snap and press fit structures, detent mechanisms, etc.

The proximal end of the flexible cable is provided with a display by which the user can observe the view at the distal end of the flexible cable and any structures or objects within the field of view. In addition, the proximal end of the flexible cable can optionally be provided with a video connection such as a video output jack by which auxiliary display/viewing devices, image recorders, etc. can be connected. The proximal end of the flexible cable can further be provided with any suitable data connector port by which various devices which process electrical signals, including data recording devices, can be coupled to the optical device.

The display is provided in a housing that is configured to be hand held. The housing preferably has a gripping portion and, in addition to housing the display and associated circuitry, can further house one or more batteries for powering the display, imager and illumination devices provided at the distal end of the cable. The batteries can be removable and replaceable or externally rechargeable by means of a charging port into which an external charging device can be coupled.

Figure 1:
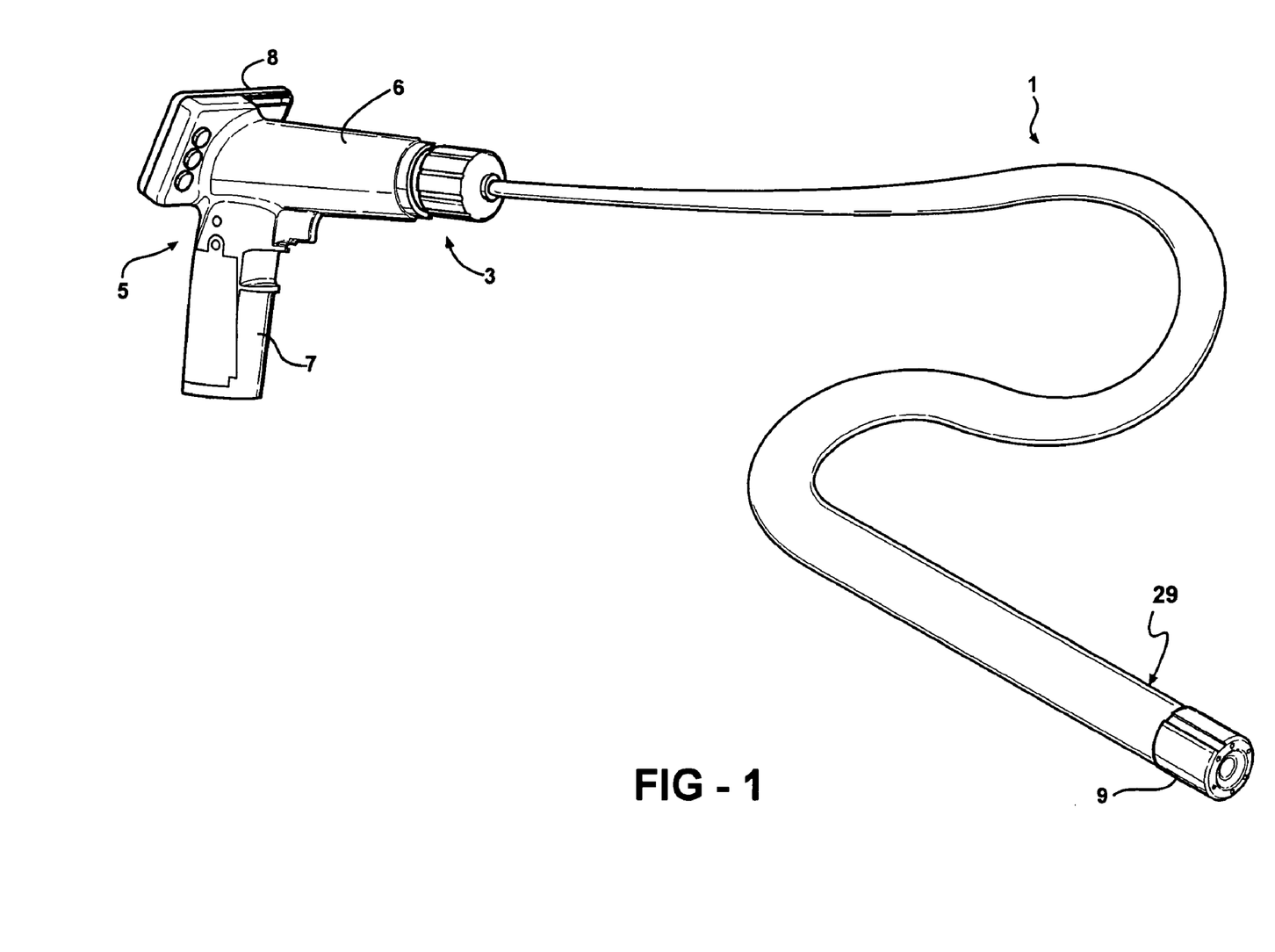
FIG. 1 is a perspective view of an optical device according to one embodiment of the present invention.

FIG. 1 is a perspective view of an optical device according to one embodiment of the present invention. The optical device of the present invention includes a flexible cable 1 having a distal end 2 and a proximal end 3. The flexible cable 1 is sufficiently rigid to allow it to be pushed though confined areas such as piping, conduits, walls, etc. The flexible cable 1 can be made from a plastic material and can either be solid (with channels for electrical wires) or hollow with sufficiently thick walls to provide a desired degree of flexibility/rigidity. For purposes of the present invention a flexible cable 1 formed in the style of a wound spring (referred to as a "gooseneck" structure) has been determined to be suitable especially when coated with an outer layer of a plastic material which reduces friction and allows the flexible cable to slide easily in confined areas and by objects and prevents the flexible cable 1 from scratching or marring adjacent surfaces that are contacted during use.

The distal end 2 of the flexible cable 1 depicted in FIG. 1 contains optical components that are discussed in more detail below. In addition, the distal end 2 of the flexible cable 1 is configured to allow various attachments to be removable coupled thereto as discussed in more detail below.

The length of the flexible cable 1 can vary according to the manner and environment in which the optical device is to be used. For most general uses the flexible cable 1 can be from about 3 to 5 foot in length or longer. For commercial use the flexible cable 1 can be much longer than 5 foot, with lengths of from about 10 to 25 foot and more being within the scope of the present invention. The diameter of the flexible cable 1 can be from about 0.2 to 0.5 inches. Larger diameters can be used for some applications if desired and suitable.

The proximal end 3 of the flexible cable 1 is coupled to an image viewer 4. In the embodiment of the invention shown in FIG. 1 the proximal end 3 of the flexible cable 1 is coupled to a handheld viewer 5 that includes a housing 6 having a hand grip 7 that is configured to be gripped and held by the user's hand. The housing 6 further supports a display screen 8 upon which the image generated by the imager 9 at the distal end 2 of the flexible cable 1 is displayed. The display screen 8 can be a LCD or a CRT or other type of display with a LCD being particularly suitable for battery operation. The housing 6 depicted in FIG. 1 contains one or more replaceable or rechargeable batteries 10 (See FIG. 8) for illuminating the LED(s) 13 at the distal end 2 of the flexible cable 1 and powering the imager 9 and display screen 8. An auxiliary video output jack 11 can be provided on the housing 6 and used to patch the video signal to another display and/or recording device. Also shown in FIG. 1 are push button controls 12 that can be used to turn on the display screen 8, imager 9, LEDs 13, and/or adjust the brightness, contrast, etc. of the display screen 8.

Figure 2:
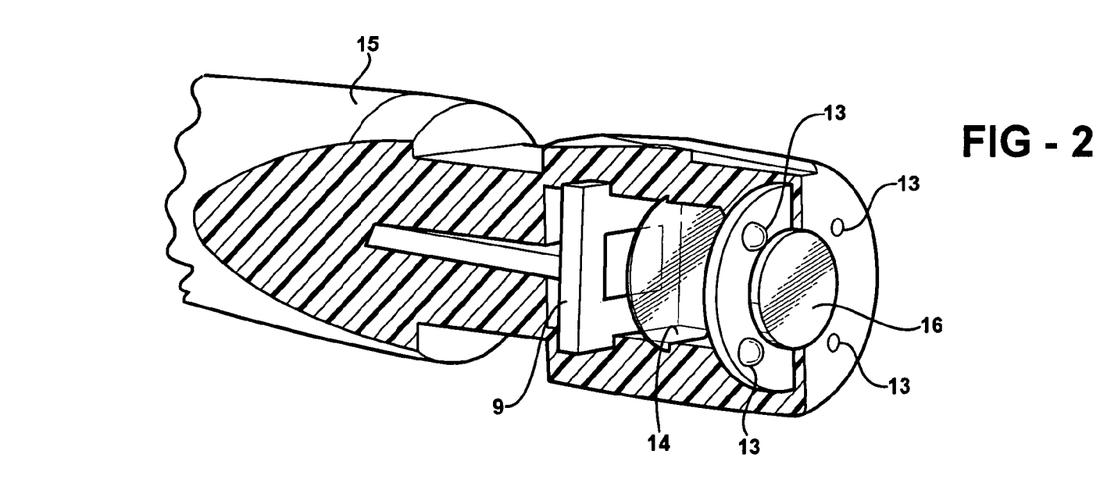
FIG. 2 is a cut away perspective view of the distal end of the optical device according to one embodiment of the present invention.

FIG. 2 is a cut away perspective view of the distal end of the optical device according to one embodiment of the present invention. The optical system provided at the distal end 2 of the flexible cable 1 includes an imager 9 that can be a CMOS or CCD imager or another type of monochrome or color imager. A lens 14 is provided in front of the imager 9 and a plurality of LEDs 13 are provided forward of the lens 14. FIG. 2 depicts the optical components as being contained and held in position in a housing 15 that seals the optical components from the external environment. At the front of the housing 15 is a window 16 through which the optical system can view beyond the end of the device.

Figure 3:
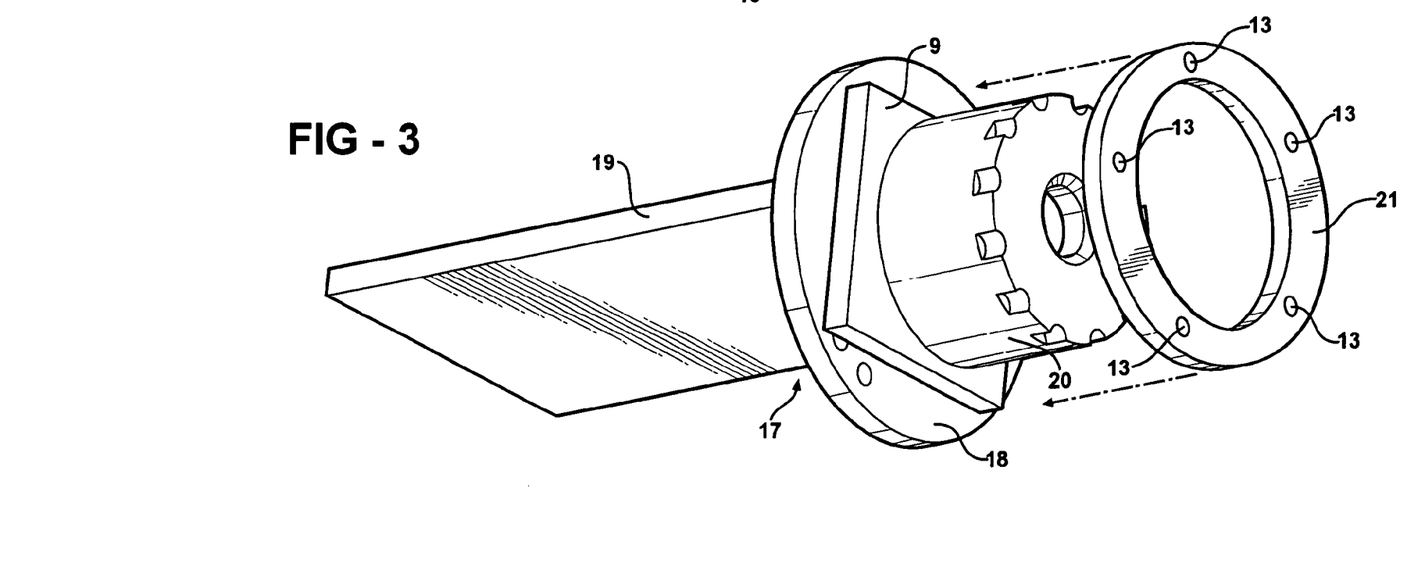
FIG. 3 is a perspective view of the optical components at the distal end of the optical device according to one embodiment.

FIG. 3 is a perspective view of the optical components at the distal end of the optical device according to one embodiment. FIG. 3 depicts how the optical components are coupled to a uniquely shaped circuit board 17. The circuit board 17 includes a base 18 from which a support 19 extends rearward. The imager 9 depicted in FIG. 3 includes a camera portion 20. The camera portion 20 receives and passes an image onto the imager 9 which is attached to the base 18 of the circuit board 17. The camera portion 20 includes an aperture at the front and lens 14 (discussed above) and blocks out extraneous light in a conventional manner In the embodiment of the invention depicted in FIG. 3 the LEDs 13 which provide illumination in front of the distal end of the device are provided on a annular shaped electronic board 21 that is configured to be placed over the camera portion 20. The annular shaped electronic board 21 is used to electrically connect the LEDs 13 to the electrical leads that extend though flexible cable 1.

Figure 4A:
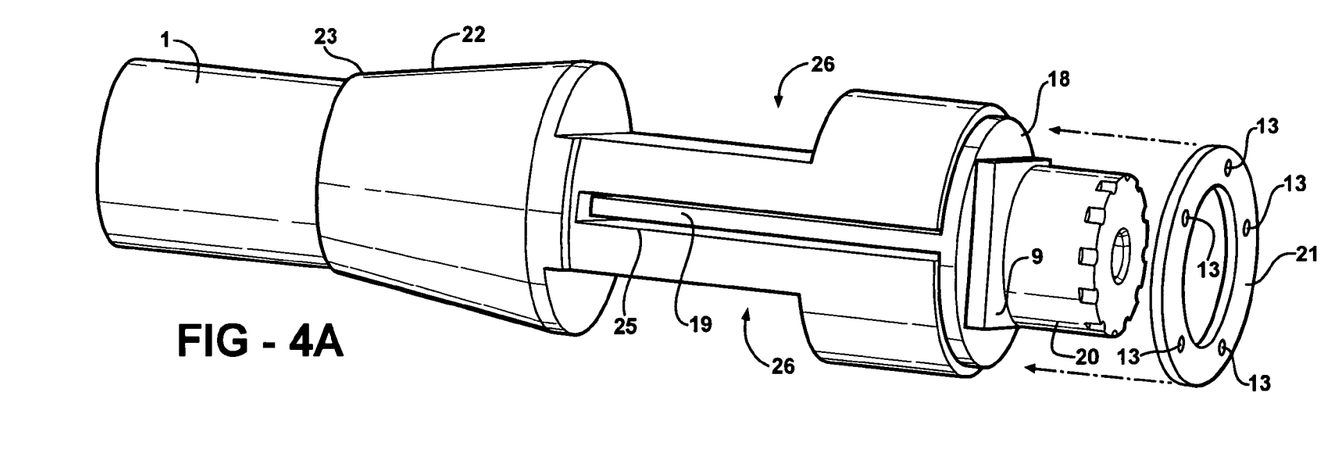
FIG. 4A is a perspective view of the optical components of FIG. 3 positioned in a supporting structure that is part of the distal end of the optical device according to one embodiment of the present invention.
Figure 5:
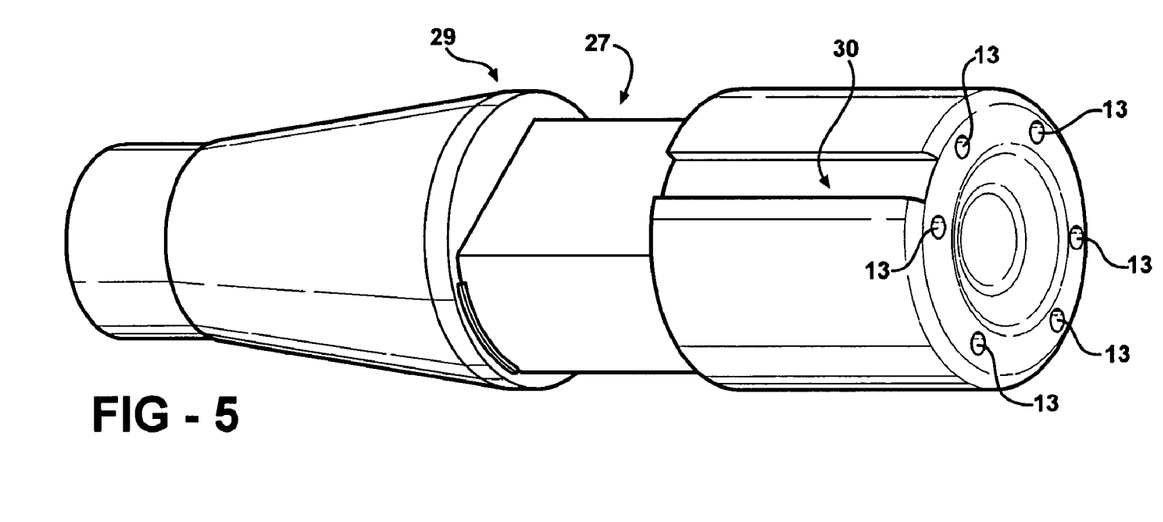
FIG. 5 is a perspective view of the distal end of the optical device after the optical components have been over molded.

FIG. 4A is a perspective view of the optical components of FIG. 3 positioned in a supporting structure that is part of the distal end of the optical device according to one embodiment of the present invention. The supporting structure 22 depicted in FIG. 4A includes a proximal end 23 that is coupled to the flexible cable 1. The distal end of the supporting structure 22 has a longitudinal slot 25 extending therein which is configured to receive the support 19 that extends rearward from the base 18 of the circuit board 17 as shown. The supporting structure 22 is configured to hold and support the components of the optical system until the assembly is over molded as shown in FIG. 5. The supporting structure 22 includes a pair of opposed notched portions 26 that are configured to provide a clip-receiving recess 27 in the final over molded structure 29 as shown in FIG. 5. The supporting structure 22 can be made of any sturdy material such as plastics, resins, metals, laminates, etc. that can support the components and withstand the over molding process.

Figure 4B:
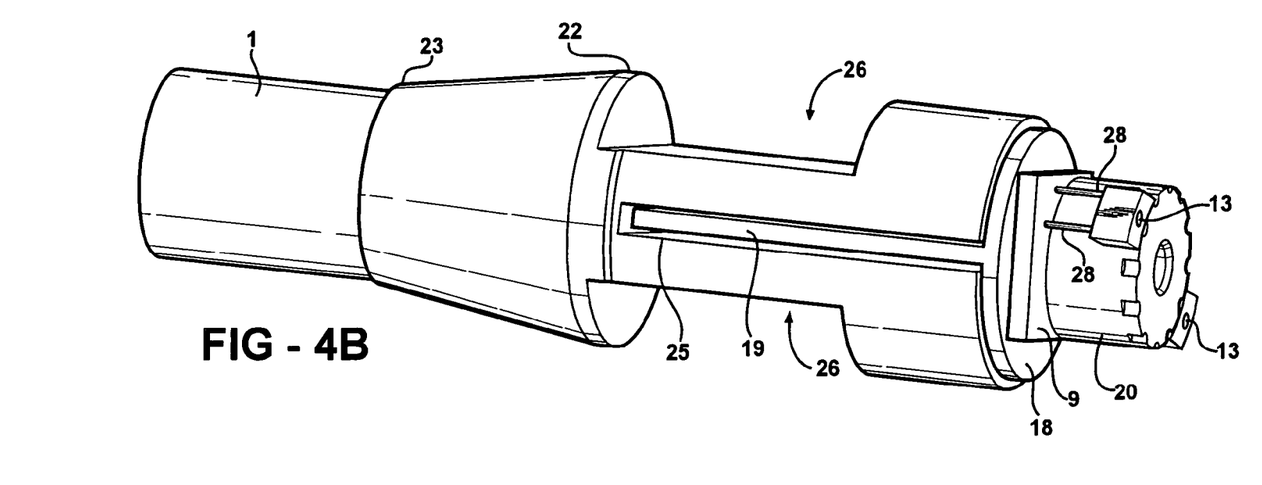
FIG. 4B is a perspective view of the optical components of FIG. 3 positioned in a supporting structure that is part of the distal end of the optical device according to another embodiment of the present invention.

FIG. 4B is a perspective view of the optical components of FIG. 3 positioned in a supporting structure that is part of the distal end of the optical device according to another embodiment of the present invention. The embodiment of the invention depicted in FIG. 4B includes two LEDs 13 that are supported in position (prior to over molding) by pins 28 that can be coupled to the circuit board 17 or any portion of the camera portion 20. In other embodiments, any convenient coupling structure such as pins, clips, temporary chemical bonding, etc. can be used to secure the individual LEDs 13 in position prior to the over molding step. Also, whereas only two LEDs 13 are depicted in FIG. 4B, it is to be understood that any number of LEDs 13 could be used, as desired.

FIG. 5 is a perspective view of the distal end of the optical device after the optical components have been over molded. Once the assembly depicted in FIG. 4A (and FIG. 4B) is over molded as shown in FIG. 5, the optical components are protected against the environment in which the device will be used. The over molded structure 29 is generally cylindrically shaped with a clip-receiving recess 27 formed over the notched portions 26 depicted in FIG. 4A (and FIG. 4B). In addition to the clip-receiving recess 27, an attachment arm recess 30 extends from the clip-receiving recess 27 to the distal end of the over molded structure 29 as shown.

Figure 6:
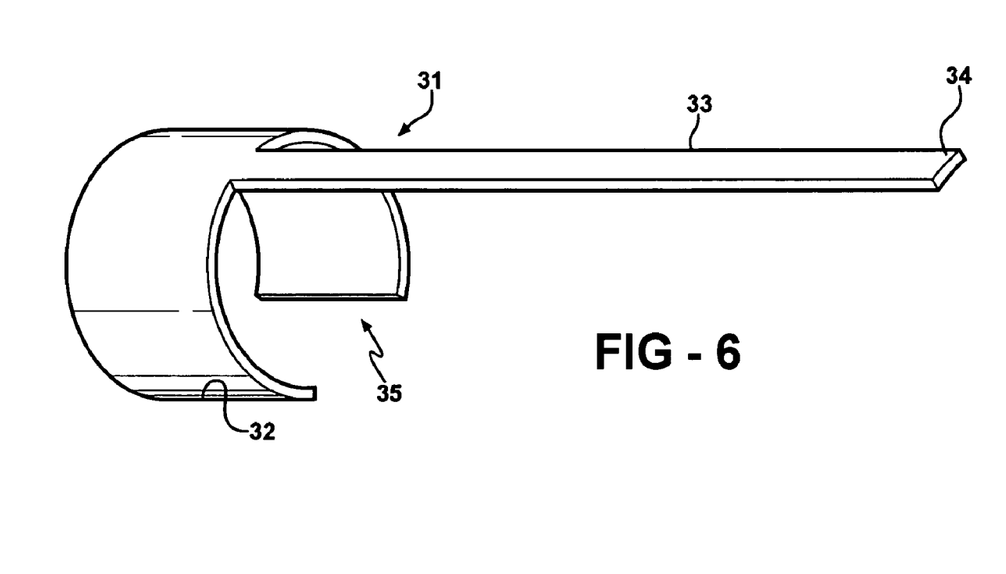
FIG. 6 is a perspective view of clip-on attachment that is configured to be coupled to the distal end of the optical device.

FIG. 6 is a perspective view of clip-on attachment that is configured to be coupled to the distal end of the optical device. The clip-on attachment 31 includes a clip portion 32, an arm 33 that extends from the clip portion 32 and a free end 34 that can have various configurations and/or structures such as hooks, loops, baskets, magnets, spears, lances, grapple or snagging devices, observational mirrors, etc. which can be manipulated to capture and retrieve various articles and/or manipulate various articles within remote situs.

The clip portion 33 comprises a cylindrical band having a gap 35 formed therein. The gap 35 has a width that is configured to pass over the structure of the clip-receiving recess 27 formed over the notched portions 26. Once the clip portion 32 passes over the structure of the clip-receiving recess 27 formed over the notched portions 26, it can be rotated about the central axis of the over molded structure 29 until the arm 33 snaps into the attachment arm recess 30. In this position, the width of gap 35 is narrower that the width of the structure of the clip-receiving recess 27 formed over the notched portions 26, so that the clip-on attachment 31 cannot become unattached or fall off the distal end of the device.

Figure 7:
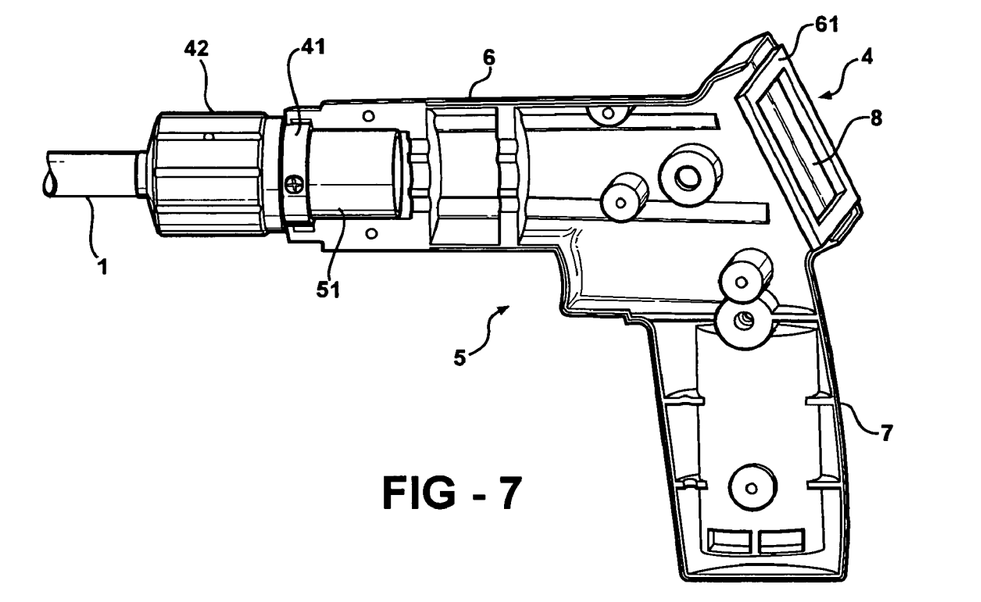
FIG. 7 is a partial sectional view of a handheld viewer provided on the proximal end of the device according to one embodiment of the present invention.
Figure 8:
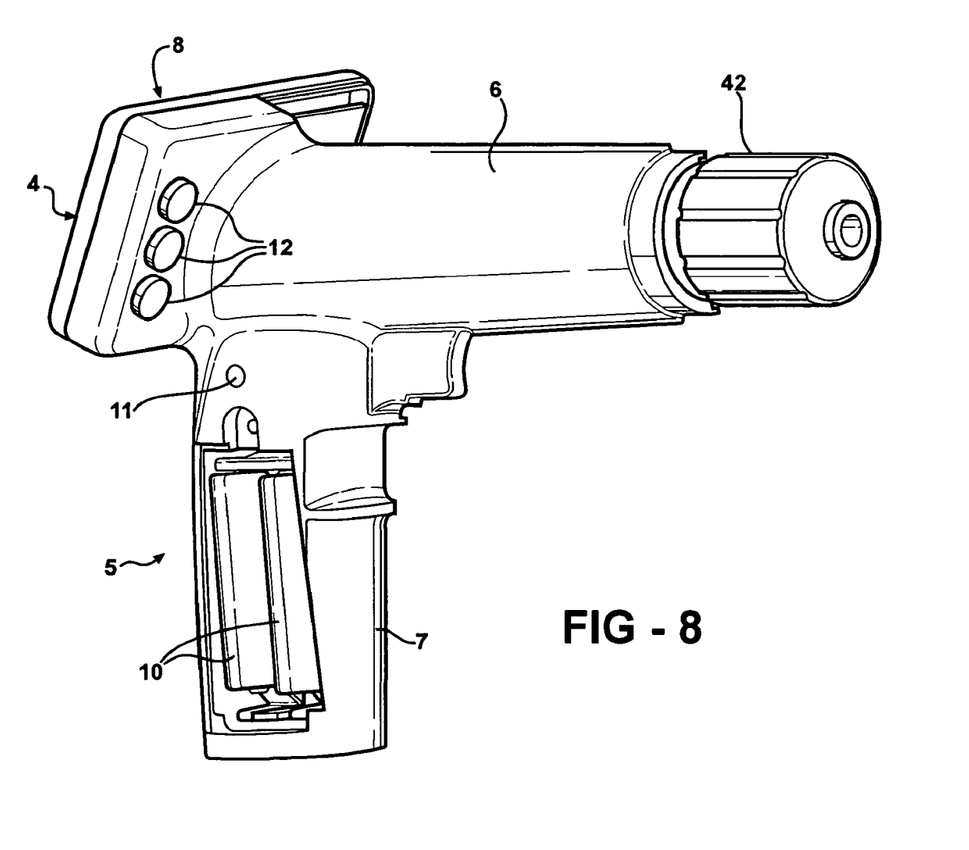
FIG. 8 is a perspective view of the handheld viewer taken from the back side of FIG. 7.

FIG. 7 is a partial sectional view of a handheld viewer provided on the proximal end of the device according to one embodiment of the present invention. FIG. 8 is a perspective view of the handheld viewer taken from the back side of FIG. 7. As discussed above, the handheld viewer 5 includes a housing 6, which according to the embodiment depicted in FIG. 7 is a two-piece housing the half portions of which can be coupled together by screws, bolts, clips, snap-fit connections, etc. In FIG. 7 only one piece or half portion of the housing 6 is shown. The housing 6 includes a hand grip 7 that is configured to be gripped and held by the user's hand. The housing 6 further supports a display screen 8 upon which the image generated by the imager 9 at the distal end 2 of the flexible cable 1 is displayed. As discussed above, the display screen 8 can be a LCD or a CRT or other type of display with a LCD being particularly suitable for battery operation. The housing 6 depicted in FIG. 7 includes an area 36 for receiving and holding one or more replaceable or rechargeable batteries 10 (See FIG. 8) for illuminating the LED(s) 13 at the distal end 2 of the flexible cable 1 and powering the imager 9 and display screen 8. As shown in FIG. 8, an auxiliary video output jack 11 can be provided on the housing 6 and used to patch the video signal to another display and/or recording device. Also shown in FIG. 8 are push button controls 12 that can be used to turn on the display screen 8, imager 9, and LEDs 13, and/or adjust the brightness, contrast, etc. of the display screen 8.

The flexible cable 1 is coupled to housing 6 at a front end of the housing, opposite the hand grip 7, in a manner that allows relative rotation between the flexible cable 1 and the housing 6. This allowance for relative rotation between the flexible cable 1 and the housing 6 enables the handheld viewer 5 to be held stationary for viewing purposes, while manipulating, i.e. rotating the flexible cable 1 to overcome, manipulate or retrieve obstacles at the distal end of the device.

Figure 9:
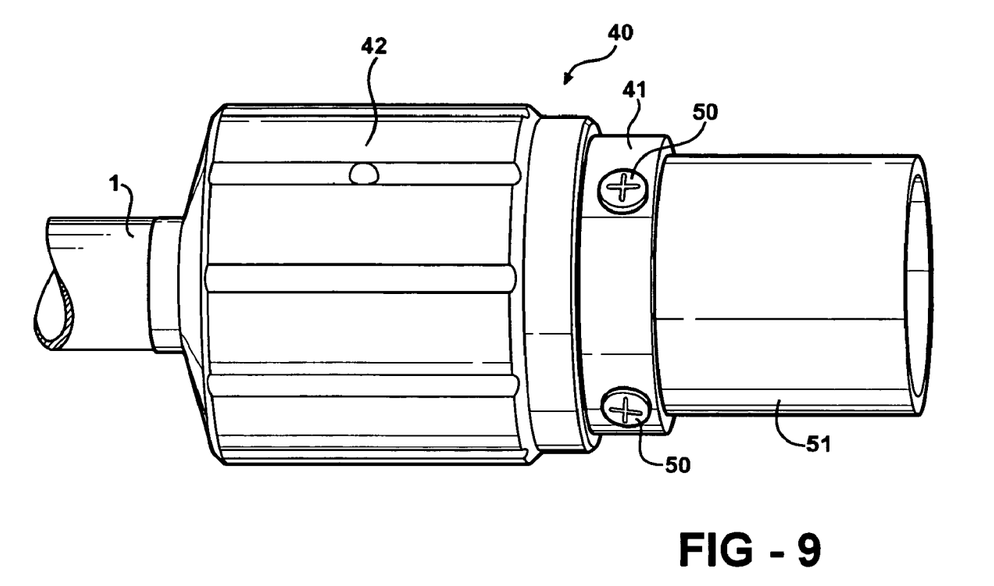
FIG. 9 is a side view of the coupling assembly used to couple the flexible cable to the handheld viewer according to one embodiment of the present invention.
Figure 10:
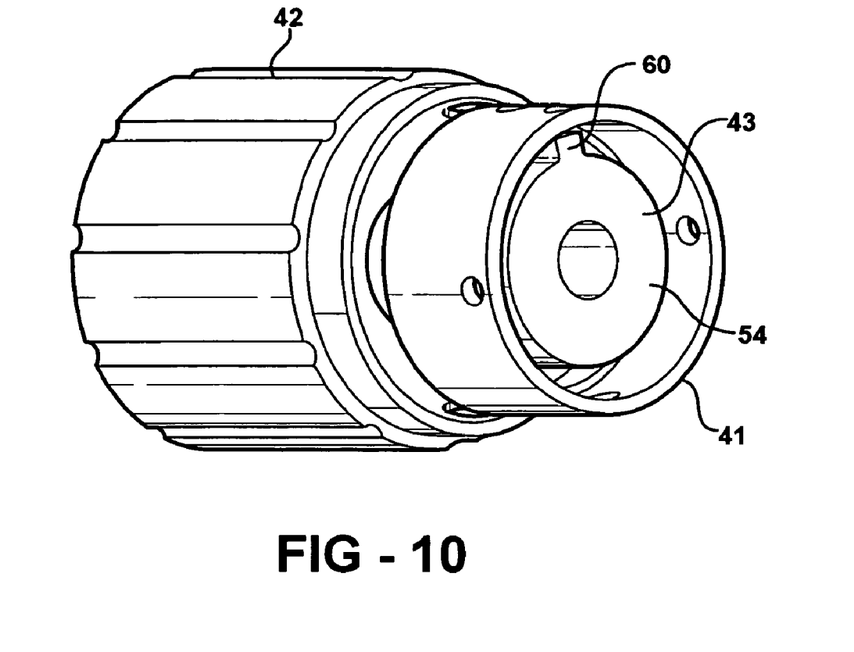
FIG. 10 is a perspective view of the coupling assembly of FIG. 9.
Figure 11:
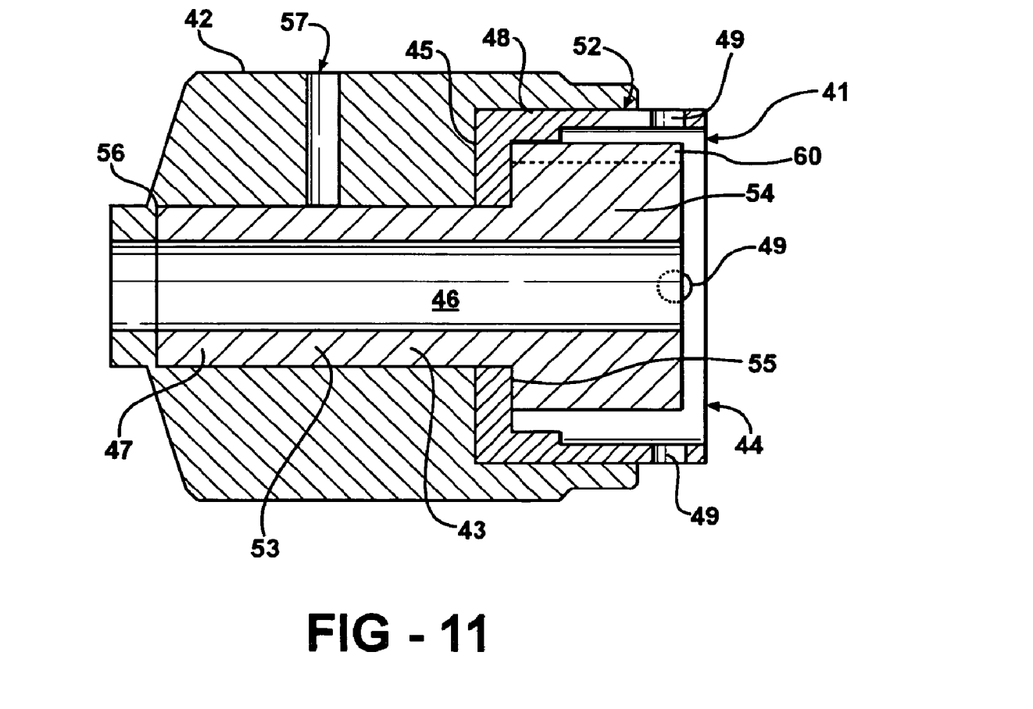
FIG. 11 is a cross sectional side view of the coupling assembly of FIG. 9.

FIG. 9 is a side view of the coupling assembly used to couple the flexible cable to the handheld viewer according to one embodiment of the present invention. FIG. 10 is a perspective view of the coupling assembly of FIG. 9. FIG. 11 is a cross sectional side view of the coupling assembly of FIG. 9.

The flexible cable 1 is rotatably coupled to the housing 6 by a coupling assembly 40 that includes an inner collar 41 that is configured to be secured in the distal end of the housing 6, an outer collar 42 that extends outward from the distal end of the housing 6 and is rotatable with respect to the housing 6, and a rotatable coupler 43 that extends through both inner collar 41 and outer collar 42. The inner collar 41 comprises a cylindrical shaped structure having a open rearward end 44 and a forward end 45 that has a central opening 46 therein which central opening 46 is configured to receive the forward end 47 of the rotatable coupler 43 therein. The cylindrical wall 48 of the inner collar 41 includes a plurality of through-holes 49 near the reward end thereof through which threaded members 50 (See FIG. 9) can pass to couple the inner collar 41 to a sleeve 51 that can in turn be attached to either or both portions of the two-piece housing 6 by suitable threaded fasteners (not shown). Through-holes 49 can be internally threaded to receive threaded members 50 if desired. An additional through-hole 52 is provided in the cylindrical wall 48 of the inner collar 41 midway along the length of the inner collar 41. A threaded member (not shown) extending through through-hole 52 provides a stop which limits the rotation of the rotatable coupler 43 as discussed in more detail below.

The rotatable coupler 43 comprises a cylindrically shaped portion 53 having a radially outward directed flange 54 on the rearward end that forms a shoulder 55. The cylindrically shaped portion 53 of the rotatable coupler 43 extends through the central opening 46 provided in the forward end of the inner collar 41. The shoulder 55 of the rotatable coupler 43 abuts the inner portion of the inner collar 41 in which the central opening 46 is formed as shown in FIG. 11.

The outer collar 42 comprises a generally cylindrical shaped structure having a central bore 56 into which the cylindrically shaped portion 53 of the rotatable coupler 43 extends as shown in FIG. 11. A threaded through-hole 57 extends through one side of the outer collar 42 and intersects the central bore 56. A threaded fastener (not shown) can extend into through-hole 57 and tightened against the cylindrically shaped portion 53 of the rotatable coupler 43. In this manner, the rotatable coupler 43 is rotatable within and with respect to inner collar 41 (which is fixed with respect to the housing 6 of the handheld viewer 5 by sleeve 51) and outer collar 42 is rotatable with the rotatable coupler 43. The proximal end flexible cable 1 can be attached to the outer collar 41 and/or the cylindrically shaped portion 53 of the rotatable coupler 43 and thus be rotatable with respect to the housing 6 of the handheld viewer 5. The flexible cable 1 can be attached to the outer collar 42 and/or the cylindrically shaped portion 53 of the rotatable coupler 43 using an epoxy or other suitable curable bonding material. The outer surface of the outer collar 42 can be provided with a suitable structure to enable gripping and rotation thereof, such as the grooved surface pattern depicted in FIG. 10.

In order to limit the rotation of the flexible cable 1 and thereby avoid twisting damage to the electrical leads that extend therethrough, the rotatable coupler 43 is provided with a stop 60 that extends radially outward from flange 54 as depicted in FIG. 10. When rotatable coupler 43 is rotated within inner collar 41 stop 60 will abut a threaded member extending through through-hole 53 and thereby prevent rotatable coupler 43 (and flexible cable 1) from rotating 360 degrees.

The inner collar 41, rotatable coupler 43, outer collar 42 and sleeve 51 can be made from any suitably mechanically strong material such as various metals, resinous materials, reinforced plastic materials, etc.

Figure 12:
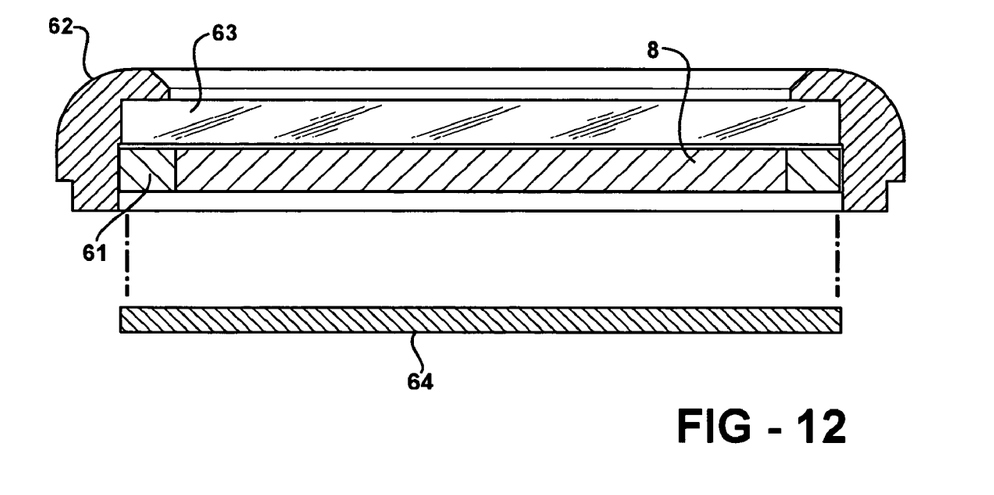
FIG. 12 is an exploded view of the display screen assembly according to one embodiment of the present invention.

FIG. 7 generally depicts the location of the image viewer 4 which is above the hand grip 7. FIG. 12 is an exploded view of the display screen assembly according to one embodiment of the present invention. The image viewer 4 includes a display screen 8 that is received in a frame 61 which frame 61 is configured to be received in a viewer cover 62 that can be coupled to the housing 6. A transparent panel 63 such as glass or scratch resistant plastic can be provided in frame 61 over display screen 8 to protect the display screen 8. As discussed above the display screen 8 can be a LCD or a CRT or other type of display with a LCD being particularly suitable for battery operation. A support panel 64 is placed in frame 61 under display screen 8 to support display screen 8 in frame 61.

FIGS. 13A-13E are side views of various clip-on attachments that can be used according to the present invention. The clip-on attachment of FIG. 13A includes clip portion 32 as shown perspectively in FIG. 6 and an arm 33 having a free end that is in the shape of a curved hook 70 that can be used to hook and retrieve objects in front of the distal end of the device.

Figures 13A, 13B:
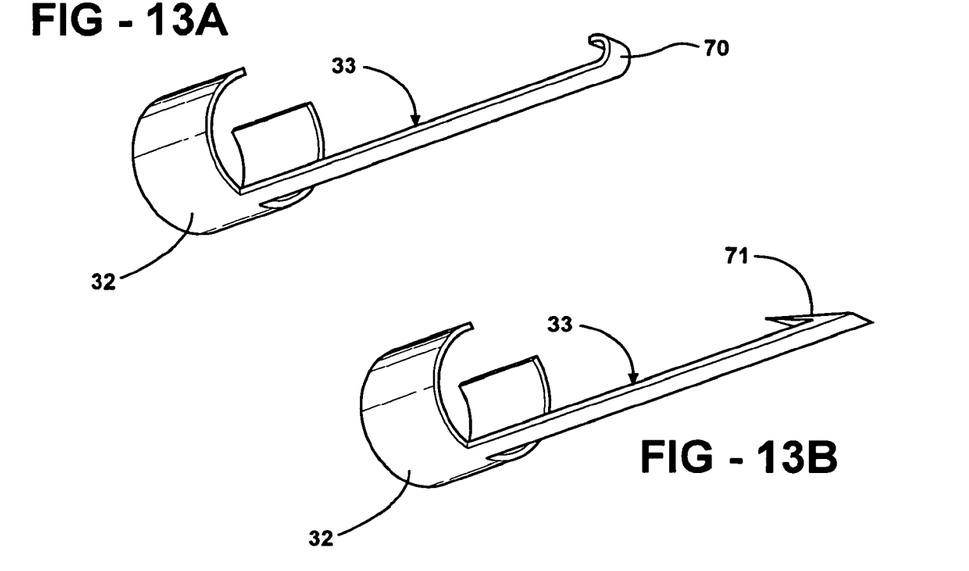
FIGS. 13A-13E are side views of various clip-on attachments that can be used according to the present invention.

The clip-on attachment of FIG. 13B includes clip portion 32 as shown perspectively in FIG. 6 and an arm 33 having a free end that is in the shape of an angled hook 71 that can be used to hook and retrieve objects in front of the distal end of the device.

Figures 13C, 13D:
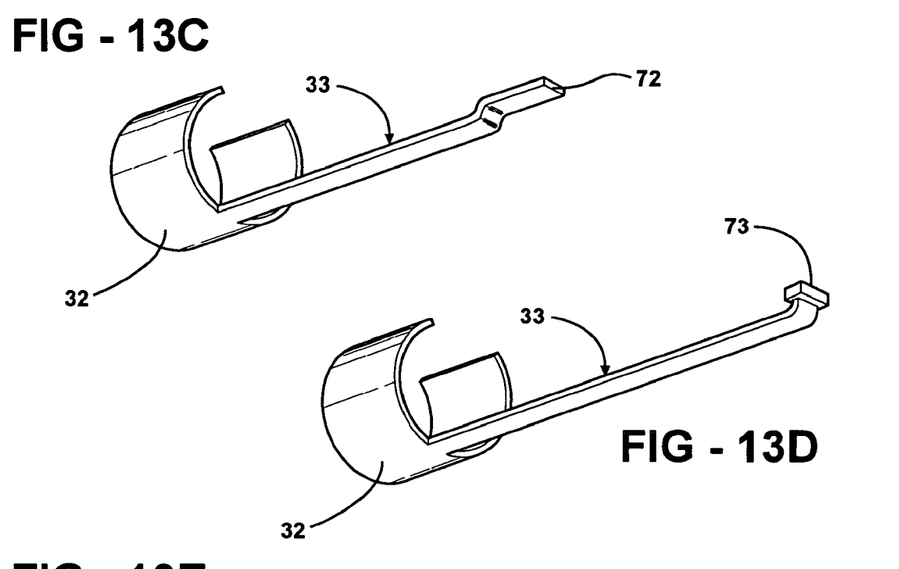

FIG. 13C shows a clip-on attachment that includes clip portion 32 as shown perspectively in FIG. 6 and an arm 33 having a free end that is provided with a leading portion 72 that is substantially parallel to the central axis of the clip portion 32, which leading portion 72 can be used to push objects in front of the distal end of the device.

FIG. 13D shows a clip-on attachment that includes clip portion 32 as shown perspectively in FIG. 6 and an arm 33 having a free end that is provided with an attachment portion 73 that can be either magnetic or coated with a sticky adhesive that can be used to capture and retrieve objects in front of the distal end of the device.

Figure 13E:
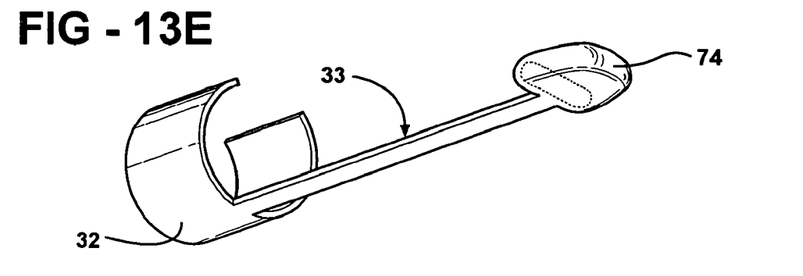

FIG. 13E shows a clip-on attachment that includes clip portion 32 as shown perspectively in FIG. 6 and an arm 33 having a free end that is provided with a basket 74 that can be used to capture and retrieve objects in front of the distal end of the device. The basket 74 can have solid walls or apertured walls or be in the form of a net if desired.

It is to be understood that FIGS. 13A-13E are non-limiting examples of various hooks, baskets, nets, magnets, spears, lances, grapple or snagging devices, observational mirrors, etc. that can be provided on the ends of clip-on attachments that can be used according to the present invention. It is also to be understood that the clip-on attachment is a non-limiting example of how the article manipulating, capturing and retrieving attachments can be coupled to the distal end of the device. In alternative embodiments the over mold structure can include spring-biased detents and the various attachments could include holes into which the spring-biased detents engage. In addition, the various attachments could merely be threaded onto the end of the over molded structure or coupled by any suitable structure or assembly, including threaded members, snap fit structures, etc.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and as set forth in the attached claims.

What is claimed is:

1. An optical device for observing a remote situs which comprises a length of flexible cable having a distal end and a proximal end;

an imager coupled to the distal end of the flexible cable for obtaining an image beyond the distal end of the flexible cable and converting the image into an electrical video signal;

a handheld image viewer coupled to the proximal end of the flexible cable for receiving the electrical video signal and converting the electrical video signal into a viewable image;

electrical leads that extend between the distal and proximal ends of the flexible cable to transfer the electrical video signal from the imager to the image viewer; and at least one article manipulation attachment that is removably coupled to a cylindrical housing which houses the imager the distal end of the flexible cable for manipulating an object located near the distal end of the flexible cable, the attachment having a finger portion which extends in parallel to a longitudinal axis of the cylindrical housing and beyond an outwardly facing end of the housing, wherein the attachment further includes a clip that attaches to the cylindrical housing and the cylindrical housing provides an annular recess, formed as an indentation in a circumference of the cylindrical housing, to receive the clip of the attachment.

2. An optical device for observing a remote situs according to claim 1, wherein the imager comprises a CMOS or a CCD.

3. An optical device for observing a remote situs according to claim 1, wherein the image viewer includes a housing having a first portion that supports a display screen and a hand grip portion.

4. An optical device for observing a remote situs according to claim 1, wherein the at least one article manipulation attachment comprises one of a hook, basket, net, magnet, adhesive portion, spear, lance, grapple device, snagging device, mirror, or pushing portion.

5. An optical device for observing a remote situs according to claim 1, further comprising at least one LED at the distal end of the device.

6. An optical device for observing a remote situs according to claim 1, wherein the at least one article manipulation attachment comprises one of a hook, basket, net, magnet, adhesive portion, spear, lance, grapple device, snagging device, mirror, or pushing portion.

7. An optical device for observing a remote situs according to claim 1, further comprising at least one LED at the distal end of the device.

8. A remote inspection device, comprising:
a flexible cable having a proximal end and a distal end;
a substantially cylindrical camera housing concentrically aligned with and coupled to a distal end of the flexible cable;
an imaging device embedded in the camera housing and operable to capture an image of a viewing area proximate to the distal end of the flexible cable and convert the image into a video signal
a light source disposed proximate to the imaging device and operable to illuminate the viewing area;
a display housing coupled to the proximate end of the flexible cable and configured to be grasped by a user of the device, wherein the display housing includes a display device adapted to receive the video signal from the imaging device and operable to convert the video signal into an image;
a portable power source located in the display housing for providing electrical power to the device;
a plurality of wires located in the flexible cable to provide electrical power from the portable power source to the imaging device and the light source, and transmit the video signal from the imaging device to the display device; and
an attachment that removably couples to the cylindrical camera housing, the attachment having a finger portion which extends in parallel to the axis of the cylindrical camera housing and beyond an outwardly facing end of the housing, wherein the attachment further includes a clip that attaches to the cylindrical housing and the cylindrical imager housing provides an annular recess, formed as an indentation in a circumference of the cylindrical housing, to receive the clip of the attachment.

9. The remote inspection device of claim 8 wherein the cylindrical imager housing includes two opposing cutaways formed in the annular recess of the imager housing and a radial surface interposed between each of the opposing cutaways, and the clip of the attachment is further defined as a cylindrical band having a radial gap formed therein, where the radial gap is larger than the radial surface of the imager housing.

10. The remote inspection device of claim 9 wherein the cylindrical imager housing further includes a locking groove formed in the radial surface thereof and extends in parallel to the axis of the cylindrical imager housing, where the locking groove is sized to receive the finger portion of the attachment.

11. A remote inspection device, comprising:
a flexible cable having a proximate end and a distal end;
a substantially cylindrical imager housing concentrically aligned with and coupled to a distal end of the flexible cable;
an imaging device embedded in an outwardly facing end of the cylindrical imager housing, the imaging device operable to capture an image of a viewing area proximate to the distal end of the flexible cable and convert the image into a video signal;
one or more light sources protruding from the outwardly facing end of the cylindrical imager housing along a perimeter of the imaging device such that the imaging device is recessed between the light sources;
a display housing coupled to the proximate end of the flexible cable and configured to be grasped by a user of the device, where the display housing includes a display device adapted to receive the video signal from the imaging device and operable to convert the video signal to a video image; and
an attachment that removably couples to the cylindrical imager housing, the attachment having a finger portion which extends in parallel to the axis of the cylindrical imager housing and beyond an outwardly facing end of the housing, wherein the attachment further includes a clip that attaches to the cylindrical housing and the cylindrical imager housing provides an annular recess, formed as an indentation in a circumference of the cylindrical housing, to receive the clip of the attachment.

12. The remote inspection device of claim 11 wherein the light sources are further defined as light emitting diodes.

13. The remote inspection device of claim 11 wherein the cap is made of a transparent plastic.

14. The remote inspection device of claim 11 wherein the cap is ultrasonic welded to the imager housing.

15. The remote inspection device of claim 11 wherein the housing display having a shape of a pistol.

16. The remote inspection device of claim 11 wherein the housing display having a handle portion configured to be grasped by a user of the device and a protruding portion extending away from the user when grasped by the user, such that the protruding portion form an obtuse angle relative to the handle portion of the housing display.

17. The remote inspection device of claim 11 wherein the flexible cable is constructed from a cylindrical conduit.

18. The remote inspection device of claim 11 wherein the display device is further defined as a liquid crystal display.

19. The remote inspection device of claim 11 wherein the cylindrical imager housing includes two opposing cutaways formed in the annular recess of the imager housing and a radial surface interposed between each of the opposing cutaways, and the clip of the attachment is further defined as a cylindrical band having a radial gap formed therein, where the radial gap is larger than the radial surface of the imager housing.

20. The remote inspection device of claim 19 wherein the cylindrical imager housing further includes a locking groove formed in the radial surface thereof and extends in parallel to the axis of the cylindrical imager housing, where the locking groove is sized to receive the finger portion of the attachment.

21. The remote inspection device of claim 11 further includes an accelerometer disposed in the imager housing and operable to report orientation of the imager housing in relation of a gravity vector, and a microprocessor disposed in the display housing, wherein the microprocessor is adapted to receive the video signal from the imaging device and the orientation data from the accelerometer and operable to orientate the video signal in relation to the gravity vector.

* * * * *

UNITED STATES PATENT AND TRADEMARK OFFICE
CERTIFICATE OF CORRECTION

| | | |
|---|---|---|
| PATENT NO. | : 7,758,495 B2 | Page 1 of 1 |
| APPLICATION NO. | : 11/328603 | |
| DATED | : July 20, 2010 | |
| INVENTOR(S) | : Alfred A. Pease et al. | |

It is certified that error appears in the above-identified patent and that said Letters Patent is hereby corrected as shown below:

Column 9,

Line 10, delete "the distal end of the flexible cable".

Signed and Sealed this
Twenty-sixth Day of July, 2011

David J. Kappos
*Director of the United States Patent and Trademark Office*